United States Patent

Saito et al.

Patent Number: 5,081,239
Date of Patent: Jan. 14, 1992

[54] RUTHENIUM CATALYZED PROCESS FOR PREPARING 4-ACETOXYAZETIDINONES

[75] Inventors: Takao Saito, Yokohama; Hidenori Kumobayashi, Chigasaki, both of Japan

[73] Assignee: Takasago International Corporation, Tokyo, Japan

[21] Appl. No.: 442,588

[22] Filed: Nov. 29, 1989

[30] Foreign Application Priority Data

Nov. 29, 1988 [JP] Japan .................. 63-301706

[51] Int. Cl.⁵ .................. C07D 205/08; C07B 41/12
[52] U.S. Cl. .................. 540/357
[58] Field of Search .................. 540/357

[56] References Cited

U.S. PATENT DOCUMENTS 4,739,084  4/1988  Takaya et al. .................. 556/21

FOREIGN PATENT DOCUMENTS

171064A1   2/1986   European Pat. Off. .
247378A1  12/1987   European Pat. Off. .
0209385   11/1988   European Pat. Off. .
63-290862 11/1988   Japan .................. 540/200
2111496A   7/1983   United Kingdom .

OTHER PUBLICATIONS

Ikariya et al., *J. Chem. Soc., Chem. Commun.*, 1985, 922–924.
*Heterocycles*, 17, 463–506 (1982).
*J. Organic Synthetic Chem.*, 41, 62 (1983).
*Tetrahedron Letters*, 23, 2293 (1982).
*Tetrahedron Letters*, 29, 1409 (1988).
*Ber.*, 92, 1599 (1959).
*Tetrahedron Letters*, 27, 4961 (1986).

Primary Examiner—Mark L. Berch
Attorney, Agent, or Firm—Bacon & Thomas

[57] ABSTRACT

A simplified process for preparing 4-acetoxyazetidinones of formula (I):

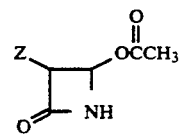

wherein Z is a hydrogen atom, a lower alkyl group or a hydroxyethyl group which may or may not be protected is disclosed. According to the invention, azetidinones of formula (II):

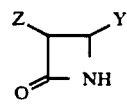

wherein Z has the same meaning as defined above and Y is a hydrogen atom or a carboxyl group is reacted with acetic acid and an oxidizing agent in the presence of a ruthenium compound as a catalyst.

3 Claims, No Drawings

RUTHENIUM CATALYZED PROCESS FOR PREPARING 4-ACETOXYAZETIDINONES

BACKGROUND OF THE INVENTION

1. Field of Invention

This invention relates to a process for preparing 4-acetoxyazetidinones of the following formula (I):

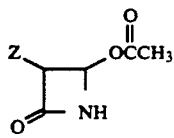

wherein Z is a hydrogen atom, a lower alkyl group or a hydroxyethyl group which may or may not be protected, which are useful as an intermediate for synthesizing penem antibiotics.

2. Description of the Background Art

Penem antibiotics such as thienamycin have recently been attracting attention as a pharmaceutical because of their wide range antibacterial spectrum.

Several preparation processes of them have already been proposed by Kametani [Heterocycles, 17, 463~506 (1982)] and by Shibuya [Journal of Organic Synthetic Chemistry, 41, 62 (1983)]. Among them, the process via 4-acetoxyazetidinones of formula (I) above is considered advantageous because different penem antibiotics are obtainable owing that the formula (I) compounds are capable of reacting various nucleophilic agents.

Conventionally known processes for preparing 4-acetoxyazetidinones (I) include a process where 4-hydroxycarbonylazetidinones are oxidized by lead tetraacetate [Tetrahedron Letters, 23, 2293 (1982)], a process where 4-hydroxycarbonylazetidinones are subjected to electrode oxidation [ibid., 29, 1409 (1988)], a process where 4-acetylazetidinones are oxidized by metachloroperbenzoic acid (Japanese Patent Application Laid-Open (Kokai) No. 50964/1986) and a process where 4-silyloxyazetidinone derivatives are reacted with acetic anhydride (European Patent No. 247,378).

In order to introduce an acetoxy group to the 4-position of azetidinones, these processes require first to form azetidinones having a specified substituent at the 4-position, then introduce an acetyl group to the substituent. This is accompanied by some drawbacks in that the preparation of the azetidinones having a specified substituent at the 4-position is cumbersome, and furthermore, conversion of the substituent at the 4-position into an acetoxy group is difficult. Accordingly, these conventional processes are not benefitial to industrial manufacturing.

Under these circumstances, the present inventors conducted extensive studies and found that a reaction with acetic acid and an oxidizing agent in the presence of a ruthenium catalyst was capable of readily introducing an acetoxy group to the 4-position of azetidinones. This invention was achieved based on this finding.

SUMMARY OF THE INVENTION

An object of this invention is to provide a process for preparing 4-acetoxyazetidinones of the following formula (I):

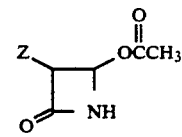

wherein Z is a hydrogen atom, a lower alkyl group or a hydroxyethyl group which may or may not be protected, which comprises reacting the following three components (a), (b) and (c):

(a) azetidinones of formula (II):

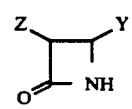

wherein Z has the same meaning as defined above and Y is a hydrogen atom or a carboxyl group, (b) acetic acid, (c) oxidizing agent, in the presence of a ruthenium compound which functions as a catalyst.

DETAILED DESCRIPTION OF THE INVENTION AND PREFERRED EMBODIMENTS

Examples of azetidinones (II) serving as the starting material of this invention include azetidine-2-one, 3-methylazetidine-2-one, 3-ethylazetidine-2-one, 3-(protected)hydroxyethylazetidine-2-one, 3-methyl-4-hydroxycarbonylazetidine-2-one, 3-ethyl-4-hydroxycarbonylazetidine-2-one, 3-(protected)hydroxyethyl-4-hydroxycarbonylazetidine-2-one. Here, as a protective group for the hydroxyl group may be mentioned those generally used for protecting the hydroxyl group of lactam compounds including silyls such as trimethylsilyl, triethylsilyl, tert-butyldimethylsilyl, diphenyl tert-butylsilyl; benzyloxycarbonyls; p-nitrobezyloxycarbonyls; and o-nitrobenzyloxycarbonyls.

Of these azetidinones (II), those where Z is a protected or unprotected hydroxyethyl group and Y is a hydrogen atom can be prepared, among others, by the following reaction scheme starting from compound (IV) which may be derived from acetoacetic acid [Ber., 92, 1599 (1959)].

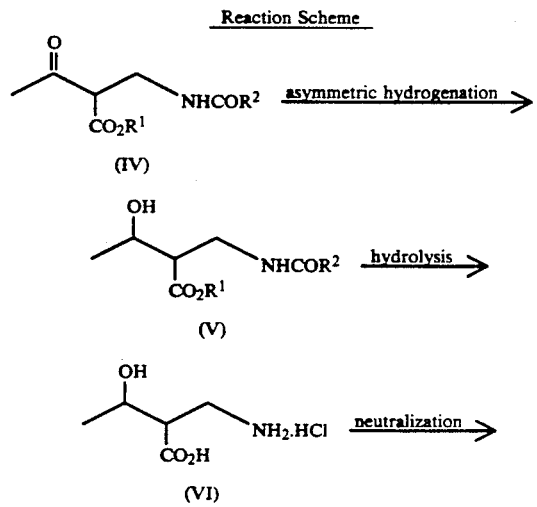

-continued
Reaction Scheme

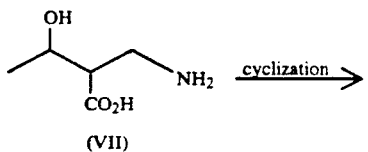

(VII)

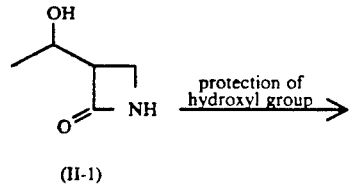

(II-1)

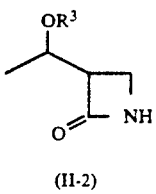

(II-2)

Here, $R^1$ is a protective group for the caboxylic acid, $R^2$ is a hydrogen atom, a lower alkyl group, a lower alkoxy group or phenyl or benzyloxy group which may be substituted by a lower alkyl group or a lower alkoxy group, and $R^3$ is a protective group for a hydroxyl group.

A lower alkyl group in this invention is defined as linear or branched alkyl group having 1-6 carbon atoms. A lower alkoxy group is defined as linear or branched alkoxy group having 1-6 carbon atoms.

Elucidating the reaction scheme, compound (IV) is first converted to compound (V) by asymmetric hydrogenation in the presence of a ruthenium-optically active phosphine complex as a catalyst. Compound (V) is then hydrolyzed by the use of diluted acid etc. to produce compound (VI), followed by neutralization to produce compound (VII). Compound (VII) is cyclized to obtain compound (II-1). Finally, protection reaction of the hydroxyl group of compound (II-1) gives compound (II-2).

The ruthenium compounds used as a catalyst in this invention are divided into categories (1), (2) and (3):

(1) $RuX_3$ (III)

wherein X is a halogen atom, a carboxyl group an acetate group or an acetylacetonate.

Examples of compound (III) include ruthenium trichloride, ruthenium tribromide, ruthenium triiodide and their hydrates; ruthenium acetylacetonate; and ruthenium acetate.

(2) Ruthenium Complexes (2-1) Ruthenium-Phosphine Complexes $HRuCl_4(PPh_3)_3$, $H_2Ru(PPh_3)_4$, $Ru_2Cl_4(BINAP)_2$-(NEt_3) $Ru_2Cl_4(Tol-BINAP)_2(NEt_3)$, $Ru(OAc)_2$-(BINAP), $Ru_2Cl_4(1,4-diphos)_2$, $HRuCl(BINAP)_2$, $[Ru(bpy)_2(O)(PPh_3)](ClO_4)_2$, $[Ru(bpy)_2(O)(PEt_3)](ClO_4)_2$, $[Ru(H_2O)(bpy)_2(PPh_3)](ClO_4)_2$, and so on. Here, "Et" stands for ethyl, "Ph" for phenyl, "Ac" for acetyl, "BINAP" for 2,2'-bis(diphenylphosphino)-1,1'-binaphthyl, "bpy" stands for bipyridyl, "Tol-BINAP" or "T-BINAP" stands for 2,2'-bis(di-p-tolylphosphino)-1,1'-binaphthyl. These abbreviations may be used throughout the specification.

(2-2) Ruthenium-Amine Complexes $[Ru(NH_3)_5Cl]Cl_2$, $Ru(NH_3)_6Cl_3$, $[Ru(C_2H_8N_2)_2(N_2)(N_3)]PF_6$, $[Ru(NH_3)_5Br]Br_2$, $[Ru(NH_3)_5I]I_2$, $[Ru(NH_3)_5(N_2)](BF_3)_2$, $[Ru(NH_3)_5(N_2)]Br_2$, $[Ru(NH_3)_5(N_2)]Cl_2$, $[Ru(NH_3)_5(N_2)]I_2$, $Ru(NH_3)_6I_3$, $RuCl_2(C_{10}H_8N_2)_2.2H_2O$, $RuCl_2(C_{10}H_8N_2)_3.6H_2O$, $Ru_3O_2(NH_3)_{14}Cl_6$, $[Ru(bpy)_2(py)(H_2O)](ClO_4)_2$, $RuO_2(py)_2(OAc)_2$, and so on.

Here, "py" stands for pyridine and this abbreviation may be used throughout the specification.

(2-3) Ruthenium-Nitrosyl Complexes $Ru(NO)Cl_3.H_2O$, $Ru(NO)(NO_3)_3$, $[RuCl(NH_3)_4(NO)]Cl_2$, $[Ru(NCO)(NH_3)_4(NO)](ClO_4)$, and so on.

(2-4) Ruthenium-Olefin Complexes $Ru(C_5H_5)_2$, $Ru[(CH_3)_5C_5]_2$, $Ru(C_8H_{12})_2$, $Ru(C_8H_{12})Cl$, $Ru(C_8H_{12})(C_8H_{10})$, and so on.

(2-5) Ruthenium-Carbonyl Complexes $Ru_3(CO)_{12}$, $[RuCl_2(CO)_3]_2$, $RuCl_2(CO)_2(PPh_3)_2$, and so on.

(2-6) Ruthenium Oxo Complexes $K[RuO_4]$, $Ba[RuO_3(OH)_2]$, and so on.

(3) Powdery Metallic Ruthenium and Ruthenium-Carriers

Ruthenium-carriers include ruthenium-carbon, ruthenium-graphite, ruthenium-alumina, ruthenium-silica-alumina, ruthenium-zeolite, ruthenium-iron oxide, ruthenium-zirconium oxide and ruthenium-diatomaceous earth.

The oxidizing agents to be used in the present invention are not limited, and mention may be given to peroxides of various carboxylic acids, other peroxides, high test hypochlorite, ozone, cyclohexene ozonides, sodium peroxide, N-methylmorpholine-N-oxide, sodium perborate, iodosylbenzenediacetate, iodosylbenzene, sodium metaperiodate and sodium paraperiodate. Examples of the peroxides of carboxylic acids include peracetic acid, perpropionic acid and m-chloroperbenzoic acid. In the practice of the present invention, commercial products may be used for the peroxides, otherwise they can be separately prepared from carboxylic acid and hydrogen peroxide. Examples of other peroxides include methyl ethyl ketone peroxide, methyl isobutyl ketone peroxide, cyclohexanone peroxide, methylcyclohexanone peroxide, diacetyl peroxide, dipropionyl peroxide and diisobutyryl peroxide. When peracetic acid is used as an oxidizing agent, acetic acid is not specifically required because peracetic acid generally contains acetic acid.

In the reaction with acetic acid in this invention, coexistence of an acetate anion is advisable for achieving a high yield. Examples of the acetate include sodium acetate, potassium acetate and lithium acetate.

In the practice of this invention, compound (II), oxidizing agent, acetic acid and ruthenium compound are dissolved or suspended in a suitable solvent, and allowed to react at a temperature ranging from $-10°$ C. to $5°$ C. for 10 minutes to 5 hours, preferably for 1 hour, under stirring. Manner and order of addition is not specifically limited, but it is desirable that the oxidizing agent be added slowly at the last step of the reaction.

Solvents usable in the present invention include acetonitrile, methylene chloride and chlorobenzene. It is desirable that the acetic acid be used 10 to 60 times, preferably 20 to 40 times mols of compound (II), and the oxidizing agent be used 1 to 8 times, preferably 2 to 3 times mols of compound (II). The ruthenium compound which will act as catalyst is used 0.01 to 0.2 times, preferably 0.02 to 0.1 times mols of compounds (II). Separation or purification of the target compound from the reaction mixture is conducted by a known method such as recrystallization or column chromatography.

As explained above, the process according to this invention has utility for the industrial manufacture of 4-acetoxyazetidinones (I) which are useful as an intermediate in the synthesis route of penem antibiotics.

EXAMPLES

This invention will now be further explained by way of the following referential examples and examples.

REFERENTIAL EXAMPLE 1

Synthesis of Ru$_2$Cl$_4$((+)-BINAP)$_2$(NEt$_3$), (di[2,2'-bis(diphenyl-phosphino)-1,1'-binaphthyl]tetrachloro-diruthenium-triethylamine)

1 g (3.56 mmol) of [RuCl$_2$(COD)]$_n$ (hereinafter, "COD" stands for 1,5-cyclooctadiene), 2.66 g (4.27 mmol) of (+)-BINAP and 1.5 g of triethylamine were added to 100 ml toluene in an atmosphere of nitrogen gas. After refluxing under heat for 10 hours, the solvent was evaporated under reduced pressure. The crystals obtained were dissolved in methylen chloride, then filtered through Celite and the filtrate was evaporated to dryness. 3.7 g of dark brown solid compound, Ru$_2$Cl$_4$((+)-BINAP)$_2$(NEt$_3$) was obtained.

| Elementary analysis: for C$_{94}$H$_{79}$Cl$_4$NP$_4$Ru$_2$ | | | | |
|---|---|---|---|---|
| | Ru | C | H | P |
| Calculated (%) | 11.96 | 66.85 | 4.71 | 7.33 |
| Found (%) | 11.68 | 67.62 | 4.97 | 6.94 |

$^1$H NMR(CDCl$_3$)δppm: 1.30–1.50(t, 6H, NCH$_2$CH$_3$) 3.05–3.30(q, 4H, NCH$_2$CH$_3$) 6.40–8.60(m, 32H, Ar-H).

REFERENTIAL EXAMPLE 2

Synthesis of methyl (2S,3R)-2-(N-bezoylaminoethyl)-3-3-hydroxybutyrate

A solution was prepared by dissolving 2.5 g (10 mmol) of methyl 2-(N-bezoylaminomethyl)-3-3-oxobutyrate and 84.5 mg (0.05 mmol) of the ruthenium-optically active phosphine complex prepared by following the general procedures of Referential Example 1 (Ru$_2$Cl$_4$((+)-BINAP)$_2$(NEt$_3$)) in 17.5 ml of methylene chloride. The solution was placed in a 100 ml stainless steel autoclave which inside air was replaced with nitrogen gas in advance. Reaction was allowed to proceed at 50° C., under a hydrogen pressure of 100 kg/cm$^2$ for 20 hours under stirring. The solvent was distilled off and the remainder was subjected to the silica gel column chromatography (eluent; mixture of n-hexane and ethyl acetate) for removal of the catalyst to obtain 2.25 g of the title compound (yield: 90%, optical purity: 98% ee). To determine the optical purity, the compound was further derived to an ester of (+)-α-methoxy-α-trifluoromethylphenyl acetic acid, then applied to high performance liquid chromatography (column; Develosil ® 100-3 (4.6 mm×250 mm), manufactured by Nomura Kagaku K. K.; wavelength (UV): 254 nm; eluent: hexane/diethylether=90/10; flow rate: 1 ml/min).

$^1$H NMR (CDCl$_3$)δppm: 1.26(d, J=6.25 Hz, 3H) 2.62(m, 1H), 3.57–3.62(m, 1H), 3.73(s, 3H), 4.60–4.03(m, 1H), 4.07–4.14(m, 1H), 7.02(br, s, 1H), 7.41–7.80(m, 5H).

REFERENTIAL EXAMPLE 3

Synthesis of (2S,3R)-2-aminomethyl-3-hydroxybutyric acid hydrochloride 10.65 g (42.43 mmol) of methyl (2S,3R)-2-(N-bezoylaminomethy)-3-hydroxybutyrate was added to the 70 ml of 10% aqueous HCl solution at room temperature. The mixture was refluxed for 4.5 hours, then cooled to room temperature. Precipitated benzoic acid was filtered out, the filtrate was washed twice with 100 ml toluene, and the aqueous layer was taken and concentrated under reduced pressure to obtain 6.67 g of the title compound (yield: 93%).

$^1$H NMR(CD$_3$OD)δppm: 1.32(3H, d, J=6.54), 2.85(1H, m), 3.37(2H, m), 4.33(1H, dq, J=6.54, 4.99).

REFERENTIAL EXAMPLE 4

Synthesis of (2S,3R)-2-aminomethyl-3-hydroxybutyric acid 6.14 g (36.22 mmol) of (2S,3R)-2-aminomethyl-3-hydroxybutyric acid hydrochloride was added with 150 ml of acetonitrile, and further added, while cooled in ice, with 5.05 ml (36.22 mmol) of triethylamine, then subjected to a vigorous stirring for 2 days at room temperature. Powdery crystals precipitated were collected, washed with 100 ml of acetonitrile and filtered to obtain 4.07 g of the title compound in crystals (yield: 84%).

$^1$H NMR(CD$_3$OD)δppm: 1.27(3H, d, J=6.39), 2.49(1H, dt, J=6.21, 6.36), 3.26(2H, d, J=6.36), 4.10(1H, dq, J=6.21, 6.39).

REFERENTIAL EXAMPLE 5

Synthesis of (1'R,3S)-3-hydroxyethylazetidine-2-one 2.28 g (17.14 mmol) of (2S,3R)-2-aminomethyl-3-hydroxybutyric acid was added with 342 ml of dried acetonitrile to prepare a suspension, to which 5.49 g (20.93 mmol) of triphenylphosphine and 4.54 g (20.61 mmol) of dipyridyldisulfide were further added and allowed to react at 55° C.-60° C. over 20 hours. The product was concentrated under reduced pressure, then applied to silica gel column chromatography for isolating and purifying the title compound by the use of methylene chloride—ethyl acetate—methanol (8:8:1). 1.64 g of the purified title compound was obtained (yield: 83%).

$^1$H NMR(CDCl$_3$)δppm: 1.28(3H, d, J=6.3), 2.10(1H, —OH), 3.31(1H, ddd, J=5.4, 5.2, 2.7), 3.36(2H, ddd, J=5.2, 5.2, 2.7), 4.21(1H, dq, J=6.3, 5.4), 5.82(1H, —NH)

REFERENTIAL EXAMPLE 6

Synthesis of (1'R,3S)-3-(1'-tert-butyldimethylsilyloxyethyl)azetidine-2-one 3.88 g (33.74 mmol) of (1'R,3S)-3-hydroxyethylazetidine-2-one was added with 15 ml of dried DMF ("DMF" stands for dimethylformamide) to dissolve, then further added with 2.41 g (35.43 mmol) of imidazole and 5.34 g (35.43 mmol) of tert-butyldimethylsilylchloride for reaction at room temperature over 20 hours. The reaction mixture was poured into 100 ml of cold water, then precipitated crystals were collected by filtration to obtain 6.5 g of the title compound (yield: 84%).

[α]$_D^{25}$ −69.8° (c=1.02 CHCl$_3$)

Optical Purity: 94% ee m.p. 66°–68° C.

$^1$H NMR(CDCl$_3$)δppm: 0.09(6H, s), 0.88(9H, s), 1.21(3H, d, J=6.21), 3.21(1H, m), 3.30(1H, dd, J=5.08, 5.26), 3.37(1H, m), 4.20(1H, dq, J=5.26, 6.21), 5.63(1H, —NH).

EXAMPLE 1

Synthesis of (1′R,3R,4R)-4-acetoxy-3-(1′-tert-butyldimethylsilyloxyethyl)azetidine-2-one 0.50 g (2.18 mmol) of (1′R,3S)-3-(1′-tert-butyldimethylsilyloxyethyl)azetidine-2-one was dissolved in 20 ml of dried acetonitrile in a stream of nitrogen gas and further added with 0.18 g (2.18 mmol) of sodium acetate. This solution was added with 20 ml of dried acetonitrile solution containing 45 mg (0.22 mmol) of ruthenium trichloride then cooled to −5° C., to which 3 ml of acetic acid solution containing 40% peracetic acid was carefully dropped. The solvent was distilled under reduced pressure, followed by purification by silica gel column chromatography to obtain 0.5 g of the title compound (yield: 80%).

$[α]_D^{25}$ +47.8° (c=0.98 CHCl$_3$)

Optical Purity: 99.2% ee $^1$H NMR(CDCl$_3$)δppm: 0.08(3H, s), 0.09(3H, s), 0.88(9H, s), 0.08(3H, s), 0.09(3H, s), 0.88(9H, s), 1.27(3H, d, J=6.35), 2.11(3H, s), 3.19(1H, dd, J=3.50, 1.27), 4.23(1H, dq, J=3.50, 6.35) 5.84(1H, d, J=1.27), 6.40(1H, —NH).

EXAMPLE 2

Synthesis of 4-acetoxyazetidine-2-one 0.71 g of azetidine-2-one and 0.82 g of anhydrous sodium acetate were suspended in 20 ml of acetonitrile and cooled to −5° C., to which 10 ml of acetonitrile containing 0.26 g of ruthenium trichloride.3H$_2$O was added. 3.8 ml of acetic acid containing 40% peracetic acid was carefully dropped thereto so as to maintain the temperature not higher than 0° C., then continuously stirred at 0° C. for 30 minutes. The solvent was distilled off under reduced pressure at a temperature not higher than 40° C., and subjected to silica gel chromatography (eluent: n-hexane:ethyl acetate=1:1) for purification to obtain 0.92 g of the title compound (yield 71%).

$^1$H NMR(CDCl$_3$)δppm: 2.13(3H, s), 3.00(1H, ddd, J=15.26, 1.40, 0.45), 3.26(1H, ddd, J=15.26, 4.05, 2.58), 5.84(1H, dd, J=4.05, 1.40), 7.02(1H, bs, —NH).

EXAMPLE 3

Synthesis of 4-acetoxy-3-ethylazetidine-2-one 1.0 g of 3-ethylazetidine-2-one and 0.83 g of anhydrous sodium acetate were suspended in 20 ml of methylene chloride and cooled to −5° C., to which 0.35 g of ruthenium acetylacetonate complex was added. 3.8 ml of acetic acid solution containing 40% peracetic acid was dropped thereto carefully so as to maintain the temperature not higher than 0° C., followed by the procedures in Example 2 to obtain 1.17 g of the title compound (yield: 74.5%).

$^1$H NMR(CDCl$_3$)δppm: 0.99(3H, t, J=7.4), 1.75(2H, m), 2.10(3H, s), 3.08(1H, m), 5.78(1H, d, J=1.25), 6.55(1H, bs, —NH).

EXAMPLE 4

Synthesis of (1′R,3R,4R)-4-acetoxy-3-(1′-hydroxyethyl)azetidine-2-one 0.3 g of (1′R,3S)-3-(1′-hydroxyethyl)azetidine-2-one and 0.21 g of anhydrous sodium acetate were suspended in 12 ml of methylene chloride and cooled to −5° C., to which 2 ml of acetic acid solution containing 68 mg of ruthenium trichloride.3H$_2$O was added. Thereafter, the general procedures in Example 2 were followed to obtain 155 mg of the title compound (yield: 12%). The eluent used in the silica gel column chromatography was a mixture solution of methylene chloride—ethyl acetate—methanol (20:20:1).

$^1$H NMR(CDCl$_3$)δppm: 1.25(3H, d, J=6.7), 2.08(3H, s), 3.17(1H, m), 4.16(1H, m), 5.81(1H, m), 7.09(1H, bs, —NH)

EXAMPLE 5

Synthesis of (1′R,3R,4R)-4-acetoxy-3-(1′-tert-butyldimethylsilyloxyethyl)azetidine-2-one 10.53 g of (1′R,3S)-3-(1′-tert-butyldimethylsilyloxyethyl)azetidine-2-one and 3.58 g of anhydrous sodium acetate were suspended in 400 ml of acetonitrile and cooled to 0° C., to which a 200 ml acetonitrile solution containing 1.14 g of ruthenium trichloride.3H$_2$O was added, followed by the similar procedures in Example 2 to obtain 10.5 g of the title compound (yield: 80%). The eluent used in the silica gel column chromatography was a mixed solvent of n-hexane—ethylacetate (4:1).

$^1$H NMR(CDCl$_3$)δppm: 0.08(3H, s), 0.09(3H, s), 0.88(9H, s), 1.27(3H, d, J=6.35), 2.11(3H, s), 3.19(1H, dd, J=3.50, 1.27), 4.23(1H, dq, J=3.50, 6.35), 5.84(1H, d, J=1.27), 6.40(1H, NH).

EXAMPLE 6

Synthesis of 4-acetoxyazetidine-2-one 0.3 g of 4-hydroxycarbonylazetidine-2-one, 0.43 g of anhydrous sodium acetate and 100 mg of 5% ruthenium-carbon were suspended in a mixture of 12 ml of methylene chloride and 4 ml of acetic acid and cooled to −3° C., to which 1.1 ml of acetic acid solution containing 40% peracetic acid was carefully dropped, subjected to stirring at 0° C. for 1 hour. The catalyst was separated by suction filtration, then solvent was distilled off under reduced pressure. 20 ml of n-hexane was added thereto. Undissolved matter was filtered off, the filtrate was concentrated under reduced pressure to obtain 0.37 g of the title compound (yield: 82%).

EXAMPLE 7

Synthesis of (1′R,3R,4R)-4-acetoxy-3-(1′-tert-butyldimethylsilyloxyethyl)azetidine-2-one 0.3 g of (1′R,3S,4R)-3-(1′-tert-butyldimethylsilyloxyethyl)-4-hydroxycarbonylazetidine-2-one, 0.18 g of anhydrous sodium acetate and 30 mg of 5% ruthenium-carbon were suspended in a mixture of 10 ml methylene chloride and 3 ml of acetic acid and cooled to −3° C., followed by the similar procedures in Example 6 to obtain 0.21 g of the title compound which was recrystalized from the use of 5 ml of n-hexane (yield: 66%).

EXAMPLES 8-18

Synthesis of (1'R,3R,4R)-4-acetoxy-3-(1'-tert-butyldimethylsilyloxyethyl)azetidine-2-one The procedures in Example 1 were followed except for the catalyst and reaction conditions, which are specifically indicated in Table 1.

The results are also shown in Table 1.

TABLE 1

| Example Nos. | Catalyst | Solvent | Substrate/catalyst (molar ratio) | Yield |
|---|---|---|---|---|
| 8 | RuCl$_2$(Ph$_3$P)$_3$ | benzene | 50 | 12 |
| 9 | RuH$_2$(Ph$_3$P)$_3$ | CH$_2$Cl$_2$ | 20 | 25 |
| 10 | Ru(OAc)$_2$(T-BINAP) | " | 20 | 38 |
| 11 | Ru(acac)$_3$ | " | 20 | 58 |
| 12 | RuCl$_3$.3H$_2$O | " | 10 | 85 |
| 13 | RuBr$_3$ | " | 10 | 77 |
| 14 | RuI$_3$ | " | 10 | 75 |
| 15 | Ru(NH$_3$)$_6$Cl$_3$ | " | 10 | 55 |
| 16 | Ru(NO)Cl$_3$.H$_2$O | " | 10 | 70 |
| 17 | Ru - carbon | " | (3)* | 80 |
| 18 | Ru - graphite | " | (3)* | 72 |

*Numerals in parentheses are substrate/catalyst ratio by weight.
Ph$_3$P: Triphenylphosphine
Ru(acac)$_3$: Ruthenium acetylacetonate

EXAMPLES 19-34

Synthesis of 4-acetoxyazetidine-2-one

In Examples 19 to 30, general procedures of Example 2 were followed, and in Examples 31 to 34, general procedures of Example 6 were followed except that the catalyst and the reaction conditions were changed as indicated in Table 2.

The results are also shown in Table 2.

TABLE 2

| Example Nos. | Catalyst | Solvent | Substrate/catalyst (molar ratio) | Yield |
|---|---|---|---|---|
| 19 | RuCl$_2$(Ph$_3$P)$_3$ | benzene | 10 | 48 |
| 20 | " | methylene chloride | 10 | 23 |
| 21 | Ru(OAc)$_2$(T-BINAP) | " | 20 | 35 |
| 22 | Ru(acac)$_3$ | " | 20 | 58 |
| 23 | Ru(OAc)$_3$ | " | 10 | 43 |
| 24 | Ru(OAc)$_2$(T-BINAP) | " | 100 | 36 |
| 25 | RuCl$_3$.H$_2$O | acetic acid | 10 | 55 |
| 26 | Ru(NO)Cl$_3$.H$_2$O | methylene chloride | 20 | 47 |
| 27 | RuBr$_3$ | " | 10 | 62 |
| 28 | RuI$_3$ | " | 10 | 70 |
| 29 | Ru(NH$_3$)$_6$Cl$_3$ | " | 10 | 50 |
| 30 | RuH$_2$(Ph$_3$P)$_3$ | " | 10 | 45 |
| 31 | 5% Ru—C | " | (3)* | 78 |
| 32 | 1% Ru-graphite | " | (3)* | 61 |
| 33 | Ru$_3$(CO)$_{12}$ | " | 10 | 75 |
| 34 | RuCl$_2$(COD) | " | 10 | 43 |

*Numerals in parentheses are substrate/catalyst ratio by weight.
Ph$_3$P: Triphenylphosphine
COD: 1,5-cyclooctadiene
Ru(acac)$_3$: Ruthenium acetylacetonate
Ru(OAc)$_3$: Ruthenium acetate

EXAMPLE 35

Synthesis of (1'R,3R,4R)-4-acetoxy-3-(1'-tert-butyldimethylsilyloxyethyl)azetidine-2-one 100 mg (0.44 mmol) of (1'R,3S)-3-(1'-tert-butyldimethylsilyloxyethyl)azetidine-2-one, 36 mg (0.44 mmol) of anhydrous sodium acetate and 12 mg (0.04 mmol) of ruthenium trichloride.3H$_2$O were dissolved in 1 ml of acetic acid, to which 167 mg (0.97 mmol) of m-chloroperbenzoic acid in a solid state was added by small amounts over 1 hour. After continuous stirring for 4 hours, the reaction solution was poured into 10 ml of water, then extracted twice with 50 ml of n-hexane. The combined n-hexane layers were washed with 10 ml aqueous solution of saturated sodium bicarbonate and 10 ml of saturated NaCl solution in this order, then dried over anhydrous magnesium sulfate and filtered. The solvent was distilled off under reduced pressure. Purification by silica gel column chromatography using a mixed solvent of n-hexane—ethyl acetate (4:1) produced 86 mg of the title compound (yield: 68%).

EXAMPLES 36-45

Synthesis of (1'R,3R,4R)-4-acetoxy-3-(1'-tert-butyldimethylsilyloxyethyl)azetidine-2-one The title compound was synthesised by following the procedures in Example 35 but using various oxidizing agents as indicated in Table 3.

The results are also shown in Table 3.

TABLE 3

| Example Nos. | Oxidizing agent | Substrate/Oxidizing agent (molar ratio) | Yield (%) |
|---|---|---|---|
| 36 | Cyclohexeneozonide *) | 2.2 | 67 |
| 37 | Methylethylketone peroxide | 2.2 | 78 |
| 38 | Sodium peroxide | 4.0 | 74 |
| 39 | N-methylmorpholine-N-oxide | 2.2 | 15 |
| 40 | Sodium perborate | 2.2 | 13 |
| 41 | Iodosylbenzenediacetate | 2.2 | 88 |
| 42 | Iodosylbenzene | 2.2 | 79 |
| 43 | Sodium metaperiodate | 2.2 | 17 |
| 44 | Sodium paraperiodate | 2.2 | 31 |
| 45 | High test hypochlorite | 2.2 | 13 |

*): prepared from cyclohexene treated with ozone gas in the presence of acetic acid.

EXAMPLE 46

Synthesis of (1'R,3R,4R)-4-acetoxy-3-(1'-hydroxy-ethyl)azetidine-2-one 1.0 g (8.7 mmol) of (1'R,3S)-3-(1'-hydroxy-ethyl)azetidine-2-one and 0.649 g (7.91 mmol) of anhydrous sodium acetate were added to 40 ml of methylene chloride under the nitrogen atmosphere. The mixture was cooled down to −5° C., to which 65.64 mg (0.322 mmol) of K[RuO₄] and 12.0 ml of acetic acid were added, followed by dropping thereto 3.34 g (17.58 mmol) of 40% peracetic acid over 5 to 10 minutes so as to maintain the temperature not higher than 2° C. After the dropping, the reaction mixture was maintained at −5° C. to 0° C. over 2 hours. The reaction solution was concentrated, then purified by silica gel column chromatography by the use of methylene chloride—ethyl acetate—methanol (8:8:1) to obtain 0.687 g of the title compound (yield: 45.6%).

EXAMPLE 47

Synthesis of (1′R,3R,4R)-4-acetoxy-3-(1′-hydroxy-ethyl)azetidine-2-one

General procedures in Example 46 were followed except that Ba[RuO₃(OH)₂] was used in place of K[RuO₄] as a catalyst. 102.95 mg (0.32 mmol) of the title compound was obtained (yield: 19.75%).

EXAMPLE 48

Synthesis of (1′R,3R,4R)-4-acetoxy-3-(1′-tert-butyldimethylsilyloxyethyl)azetidine-2-one 1.02 g (4.367 mmol) of (1′R,3S)-3-(1′-tert-butyldimethylsilyloxyethyl)azetidine-2-one and 0.34 g (4.146 mmol) of anhydrous sodium acetate were added to 40 ml of methylene chloride in an atmosphere of nitrogen gas. The mixture was cooled down to −5° C. and added with 32.96 mg (0.1615 mmol) of K[RuO₄] and 12.0 ml of acetic acid, to which 1.7 g (8.95 mmol) of 40% peracetic acid was dropped over 5 to 10 minutes while maintaining the temperature not higher than 2° C. After the dropping, the reaction mixture was maintained at −5° C. to 0° C. for 1 hour. The reaction solution was concentrated, added with 20 ml of ethyl acetate, further with 20 ml of aqueous solution of sodium bicarbonate to make the solution basic, then separated. The aqueous layer was extracted twice with ethyl acetate, and the extracts were combined with the ethyl acetate layer which was previously separated. The obtained ethyl acetate solution was dried by the use of anhydrous magnesium sulfate and concentrated to obtain 1.08 g of a crude title compound (yield: 38.86%).

EXAMPLE 49

Synthesis of (1′R,3R,4R)-4-acetoxy-3-(1′-tert-butyldimethylsilyloxyethyl)azetidine-2-one General procedures in Example 48 were followed except that Ba[RuO₃(OH)₂] was used in place of K[RuO₄] as a catalyst. 51.7 mg (0.162 mmol) of a crude title compound was obtained (yield: 58.8%).

EXAMPLE 50

Synthesis of (1R,3R,4R)-4-acetoxy-3-(1′-tert-butyldimethylsilyloxyethyl)azetidine-2-one 2.0 g (8.73 mmol) of (1′R,3S)-3-(1′-tert-butyldimethylsilyloxyethyl)azetidine-2-one, 0.72 g (8.78 mmol) of anhydrous sodium acetate and 93 mg (0.145 mmol) of Ru₃(CO)₁₂ were added to 100 ml of acetic acid, then allowed to react with ozone (flow rate: 3.15 g/hr; generated from oxygen flow of 90 l/hr) at room temperature over 3 hours. Thereafter, the reacted material was filtered, concentrated, added with 100 ml of ethyl acetate, neutralized with 50 ml of 5% aqueous solution of sodium bicarbonate and ethyl acetate layer was separated. The aqueous layer was extracted twice with methylene chloride, then the extracts were combined with 100 ml of ethyl acetate which was previously separated and concentrated to obtain 1.15 g of a crude title compound. The crude compound was subjected to silica gel column chromatography by the use of n-hexane—ethyl acetate (8:1) to obtain 0.05 g of a purified title compound (yield: 1.79%) and 0.21 g of the starting material, respectively.

What is claimed is:

1. A process for preparing 4-acetoxyazetidinones of the following formula (I):

wherein Z is a hydrogen atom, a lower alkyl group or a hydroxyethyl group which may or may not be protected, which comprises reacting the following three components (a), (b) and (c):

(a) azetidinones of formula (II):

wherein Z has the same meaning as defined above and Y is a hydrogen atom or a carboxyl group, (b) acetic acid, and (c) oxidizing agent, in the presence of a ruthenium compound as a catalyst represented by RuX₃, wherein X is a halogen atom, an acetate or an acetylacetonate, or represented by RuCl₂(PPh₃)₃, RuH₂(PPh₃)₃, Ru(OAc)₂(T-BINAP), Ru(NH₃)₆Cl₃, Ru(NO)Cl₃·H₂O, RuCl₂(COD), Ru₃(CO)₁₂, K(RuO₄), and Ba(RuO₃(OH)₂).

2. A process for preparing 4-acetoxyazetidinones of the following formula (I):

wherein Z is a hydrogen atom, a lower alkyl group or a hydroxyethyl group which may or may not be protected, which comprises reacting the following three components (a), (b) and (c):

(a) azetidinones of formula (II):

wherein Z has the same meaning as defined above and Y is a hydrogen atom or a carboxyl group, (b) acetic acid, and
(c) oxidizing agent, in the presence of metallic ruthenium or a ruthenium-carrier.

3. A process for preparing 4-acetoxyazetidinones according to claim 1, wherein the ruthenium compound is a ruthenium complex selected from the group consisting of
$RuCl_2(PPh_3)_3$, $RuH_2(PPh_3)_3$, $Ru(OAc)_2(T\text{-BINAP})$, $Ru(NH_3)_6Cl_3$, $Ru(NO)Cl_3 \cdot H_2O$, $RuCl_2(COD)$, $Ru_3(CO)_{12}$, $K(RuO_4)$, and $Ba(RuO_3(OH)_2)$.

* * * * *